United States Patent [19]

Rhodes et al.

[11] 4,401,646

[45] Aug. 30, 1983

[54] METHOD AND APPARATUS FOR PURIFYING MATERIALS RADIOLABELED WITH TECHNETIUM-99M

[75] Inventors: Buck A. Rhodes; David Torvestad, both of Albuquerque, N. Mex.

[73] Assignee: University Patents Inc., Norwalk, Conn.

[21] Appl. No.: 261,783

[22] Filed: May 8, 1981

[51] Int. Cl.³ .................... A61K 49/00; A61K 43/00
[52] U.S. Cl. .................................. 424/1; 424/9
[58] Field of Search ........................ 424/1, 9

[56] References Cited

U.S. PATENT DOCUMENTS

| | | | |
|---|---|---|---|
| 3,749,556 | 7/1973 | Barak et al. | 424/1 |
| 3,852,413 | 12/1974 | Cammarata | 424/1 |
| 3,902,849 | 9/1975 | Barak et al. | 424/1 |
| 4,187,285 | 2/1980 | Meeks et al. | 424/1 |
| 4,291,012 | 9/1981 | Strecker et al. | 424/1 |
| 4,305,922 | 12/1981 | Rhodes | 424/1 |
| 4,314,986 | 2/1982 | Ruddock | 424/1 |

FOREIGN PATENT DOCUMENTS 2907880 9/1979 Fed. Rep. of Germany ......... 424/1

*Primary Examiner*—Christine M. Nucker
*Attorney, Agent, or Firm*—Paul J. Cook

[57] ABSTRACT

Compositions labeled with technetium-99m are purified by passage through a filtration column which contains a reducing agent, colloidal stannous phthalate, antioxidant and a particulate solid substrate capable of binding reduced technetium and of retaining insoluble technetium such as reduced hydrolyzed technetium.

11 Claims, 2 Drawing Figures

METHOD AND APPARATUS FOR PURIFYING MATERIALS RADIOLABELED WITH TECHNETIUM-99M

BACKGROUND OF THE INVENTION

This invention relates to a method and apparatus for purifying technetium-99m radiopharmaceuticals.

Technetium-99m radiopharmaceuticals such as $^{99m}$Tc-methylene diphosphonate (MDP), $^{99m}$Tc-diethylenetriaminepenaacetic acid (DTPA) and $^{99m}$Tc-labeled proteins such as human serum albumin, tend to become contaminated with two radiochemical impurities, pertechnetate ions and hydrolyzed reduced technetium. These impurities detract from image quality and result in unnecessary radiation exposure to the patient. It is routine practice to test these radiopharmaceuticals after preparation for the presence of impurities, and if the impurity levels are found to be excessive, the lot or kit is discarded and a fresh lot or kit is prepared. Most of the commonly used technetium radiopharmaceuticals have a limited shelf life, usually three to six hours, because of the formation with time of excessive levels of these radiochemical impurities. Rejection of radiopharmaceuticals, either at time of preparation or before they are utilized, because of excessive impurity levels, is a major expense and waste of radioactive $^{99m}$Tc. For this reason, it is highly desirable to maintain these compounds as free as possible from impurities.

In compounding of Tc-labeled compounds, stannous ions are used to reduce the pertechnetate (Tc VII) to technetate (Tc IV). The Tc IV species forms complexes with various ligands, i.e., MDP, DTPA, proteins, etc. The complexes of Tc constitute the radiopharmaceutical or diagnostic radioactive tracer. On standing, dissolved oxygen in the formulation causes the stannous ions to become oxidized to stannic ions and as the concentration of stannous is reduced by the spontaneous oxidation, the Tc-complex begins to oxidize, converting the Tc IV back to Tc VII and releasing it from the complex and forming the radiochemical impurity. The presence of excess stannous ions in the formulation tends to minimize reoxidation of the technetium. Excess stannous ions, however, can enhance the formulation of reduced hydrolyzed technetium, a form of technetium which is insoluble and unavailable for complex formation.

Even by carefully controlling the concentration of stannous ions in these formulations and utilizing other antioxidants, technetium-labeled radiopharmaceuticals must be utilized in conventional diagnostic procedures very shortly after preparation because of the deterioration of these compositions due to oxidation. It would be highly desirable to provide a means for reactivating or purifying technetium radiopharmaceuticals that have been degraded by oxidation.

SUMMARY OF THE INVENTION

In accordance with this invention, compositions radiolabeled with technetium-99m and which contain oxidation degradation products are converted to useful diagnostic compositions. The technetium radiolabeled composition to be purified is contacted with a material which entraps or otherwise binds technetium-99m, such as cross-linked dextran (Sephadex or Sepharose) or cellulose or ion exchange resins which has been premixed with stannous phthalate and a secondary antioxidant such as gentistic acid, ascorbic acid, tartaric acid or mixtures thereof. This contact is effected in a closed container which has been previously purged of oxygen and under conditions such that the contaminated radiolabeled composition becomes filtered in order to entrap hydrolyzed technetium in a manner such that the pertechnetate is reduced to technetate. The purified radiolabeled composition is recovered from the contact composition substantially free of hydrolyzed technetium and containing stannous ions in a concentration to stabilize the radiolabeled composition by minimizing oxidation thereof. The present invention provides substantial advantages in that radiolabeled technetium compositions which have become degraded due to either the formation of reduced hydrolyzed technetium or because of oxidation can be recycled to form compositions that can be utilized in conventional radiolabel scanning techniques.

DESCRIPTION OF SPECIFIC EMBODIMENTS

Figure 1:
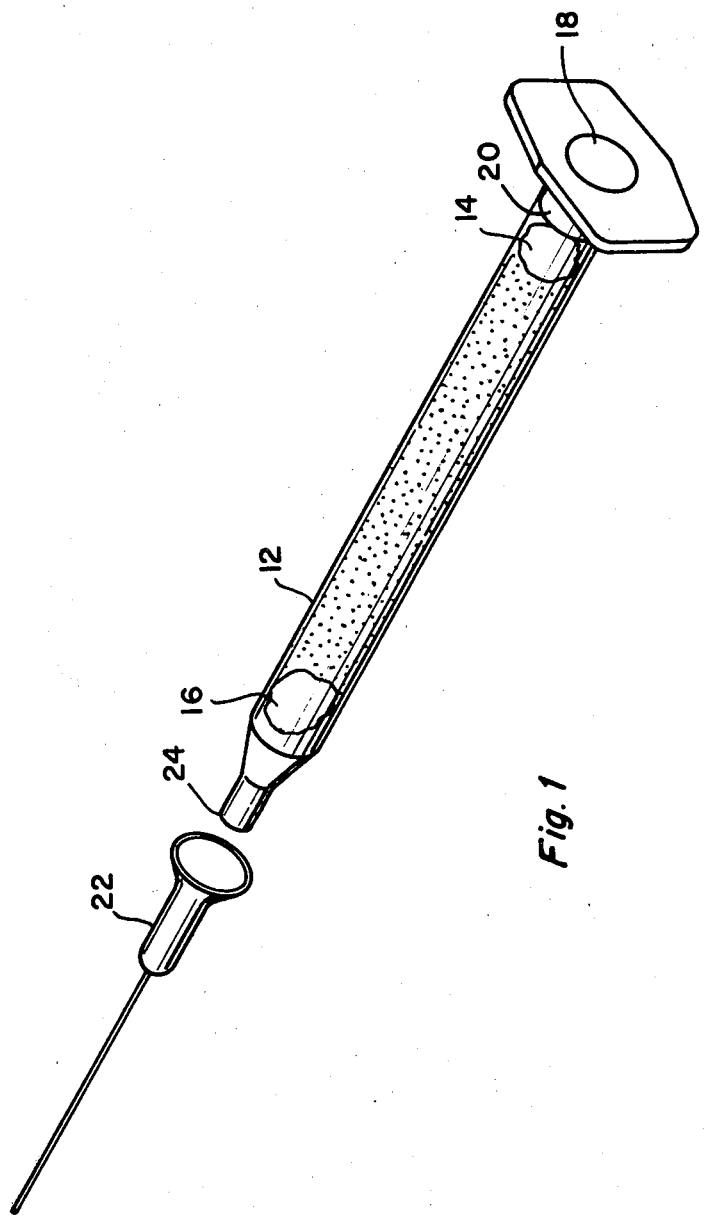
FIG. 1 is a side view of the apparatus of this invention.

The filter apparatus of this invention is prepared under a nonoxidizing atmosphere such as nitrogen, inert gas or the like utilizing reagent solutions which have been purged with a nonoxidizing gas such as nitrogen, inert gas or the like. The filter comprises a container having openings on opposite ends to permit the passage of liquid therethrough. Within the container is a particulate solid substrate capable of filtering out colloid particles from a solution and which is capable of binding technetate. A liquid composition is admixed with the substrate which has a pH between about 2.5 and about 4.0, preferably between about 3.1 and about 3.3 and which contains stannous phthalate at a concentration of at least up to the saturation point of the solution. In addition, the solution contains a secondary antioxidant at a concentration of between about 1 gm/l and about 3 gm/l, preferably at least about 2 gm/l. Suitable secondary antioxidants include gentistic acid, ascorbic acid, tartaric acid or mixtures thereof. The particulate substrate is retained within the container by means of an inert filler material positioned adjacent each opening of the container such as glass wool or cotton. After the container has been filled with the solution and the substrate in an inert atmosphere, it is sealed at both ends, such as by means of a rubber stopper, plastic cap or the like.

The apparatus of this invention is useful to remove pertechnetate and unbound reduced technetium impurities from $^{99m}$Tc-radiopharmaceuticals such as Tc-DTPA, Tc-MDP, Tc-proteins and other Tc-labeled radiopharmaceuticals wherein the bond between the techentium and the pharmaceutical molecule is moderately strong or very strong. If the bond between the technetium and the pharmaceutical molecule is weak, the technetium will be exchanged with the solid particulate substrate. The particulate bed within the filter of this invention, which has been treated with a secondary antioxidant and stannous phthalate, reduces pertechnetate, binds it and removes it from the formulation being purified. The technetium, as pertechnetate ions, are reduced in the presence of the stannous ions to Tc IV.

This species is highly reactive and will bind to the particulate substrate. Any colloid technetium species will be filtered out of the liquid formulation when the formulation is passed through the bed of particulate substrate. Thus, the particulate bed also removes the reduced hydrolyzed technetium which is one of the major radiochemical impurities. The filter is prepared with is passed through the bed of particulate substrate. Thus, the particulate bed also removes the reduced hydrolyzed technetium which is one of the major radiochemical impurities. The filter is prepared with stannous ion so that the concentration of the stannous ion in the formulation to be purified is restored but is not made excessive because of limited solubility of stannous phthalate. Thus, the concentration of stannous ion within the filter bed should be between about $2 \times 10^{-3}$ meq and about $0.1 \times 10^{-3}$ meq, preferably between about $1 \times 10^{-3}$ meq and about $0.2 \times 10^{-3}$ meq. The secondary antioxidant to the stannous ion does not interfere with the formation of complexes of technetium IV. Therefore, when a Tc-complex is passed through this filter, pertechnetate and reduced hydrolyzed technetium radiochemical impurities are removed. The concentration of stannous ion in the sample being treated is restored to an optimum level and maintained after passage through the filter by the trace of the secondary antioxidants. Therefore, a highly impure formulation, after passage through the filter, is freed of impurities and is stabilized so that it remains free of impurities for many hours. Care shoudl be taken in the manufacture of the filters to ensure that they are sterile, pyrogen-free and thus can be used for intravenous formulations. Typically, the filters are small column devices through which between about 1 and about 10 ml of a technetium-labeled formulation can be passed using disposable needles and syringes to purify and stabilize the formulation. The filters should not be used for weak technetium-complexes such as technetium-pyrophosphate, technetium-glucoheptonate or technetium-ascorbate as the technetium from these complexes may be dissociated from the complex and bound to the solid particulate filter.

Referring to FIG. 1, the filter apparatus of this invention can take the form of a disposable plastic syringe 10 which is filled with the solid particulate substrate, stannous phthalate and secondary antioxidant 12 in the manner described above. Cotton plugs 14 and 16 are provided at each end of the syringe in order to retain the particulate substrate within the syringe. One open end 18 of the syringe is closed by means of rubber plunger 20 while the other end is closed by means of syringe cap 22 which covers opening 24. In use, the radiopharmaceutical to be purified is drawn through the filter after the syringe cap 22 has been removed and a needle attached over opening 24. The attached needle then is placed into a vial of the radiopharmaceutical to be purified. A second needle which is attached to a second syringe and is inserted through rubber plunger 20 is used to draw the radiopharmaceutical from the vial through the syringe 10 and into the second syringe. The contents of the second syringe are purified and can be injected into a patient who is to be scanned in a conventional manner.

The following example illustrates the present invention and is not intended to limit the same.

EXAMPLE I

The filter was fashioned in the form of a miniature chromatographic column as shown in FIG. 1, utilizing a plastic 1 cc tuberculin syringe. A wad of glass wool or sterile cotton at each end provides a moderately secure barrier, permitting fluid flow, yet containing the filtering element. Because of the liquid content of the filter, a tight seal is required on both ends of the filter during storage. A typical syringe cap seals the luer slip tip and rubber syringe plunger seals the back end. During manufacture of the element, a $N_2$ atmosphere was maintained, and all solutions were $N_2$-purged to prevent oxidation of the reducing agents.

Sephadex G-25-80 was sterilized by boiling and cooling three times in 0.9% NaCl (sterile and pyrogen-free). The final cooling was done in the $N_2$ atmosphere so that the $O_2$ driven off with heating was replaced with the $N_2$. Water for the stannous buffer was prepared by purging a bottle of sterile water for injection (SWFI) with ultra-pure grade $N_2$ passed through a $0.22\mu$ Millipore filter. The solution was made 10 mM with respect to gentisic acid and 40 mM with respect to phthalic acid. $SnCl_2$ (1 N) was added (while maintaining a constant pH of 3.2 by back titrating with 10 N NaOH) until the solution just began to acquire some faint cloudiness. The sterilized Sephadex was washed of the saline three times with small amounts of the stannous buffer. The buffer, then, was added to the Sephadex at a volume about 5 or 10 times that of the swollen Sephadex. This was allowed to stand several hours before continuing.

Initially, a sterile, pyrogen-free glass wool plug was stuffed into the tip of the tube. Sephadex was added, much in the same way as when packing a chromatographic column, adding the Sephadex solution and allowing the excess fluid to drain. When nearly full of Sephadex, the column was capped at the tip, and a glass wool plug was placed at the end followed with the rubber plunger.

$Sn^{++}$ Output (Table 1)

An initial test was done to determine the quantity of stannous ions eluted when 0.9% NaCl is passed through the filter. The filter is eluted by attaching a needle to the syringe, inserting the needle into a vial and drawing the solution through the filter by way of the rubber seal using another hypodermic needle and syringe inserted through the rubber seal. $Sn^{++}$ was measured (by means of a potentiometric titration with iodine) in four successive 1 ml samples as they were drawn through the filter. The analysis showed a variation of up to 2 times between filters over the first ml. The variation is virtually lost by the third or fourth ml however, as $Sn^{++}$ drops to a low level which is about the same for all of the filters tested.

Removal of Tc-99m from 0.9% Saline Solution (Table 2)

Sephadex has a natural ability to bind strongly to reduced forms of Tc, but only weakly to $TcO_4^-$ (Tc VII). The $TcO_4^-$ was removed after reduction by the stannous salts upon passage through the filter. Samples of $TcO_4^-$ and reduced Tc analysis before and after passage through the filter showed that nearly all Tc-99m was removed in both cases.

Filtration of a Radiopharmaceutical (Table 3, Table 4)

To determine the effectiveness of the filter on actual radiopharmaceuticals, reconstituted MDP (medronate sodium by New England Nuclear) and DTPA (diethylenetriaminepentaacetic acid by Diagnostic Isotopes, Incorporated) kits were allowed to decay for about 48 hours.

First, the MDP and DTPA were chromatographed on a 1.5×20 cm Sephadex G-25-80 column, followed by eluting with 50 mM, pH 5.5, phthalate buffer containing $Sn^{++}$. The MDP showed only about a 53% yield of bound Tc; the DTPA showed about 87%. Several ml of each radiopharmaceutical was drawn through the filter and reanalyzed in the same way. For MDP, the return of bound Tc-99m rose to 77%, almost the same as for other good MDP yields when analyzed in the same way. The column, apparently, removes a certain portion of bound Tc depending on the strength of association between Tc and its chemical or protein carrier. Glucoheptonate, for example, is known to be a weak binding agent, and shows virtually no yield when chromatographed this way. For DTPA, a 96% return was seen from column chromatography. Apparently DTPA binds Tc strongly, the chromatographic column being unable to strip Tc from the DTPA.

Biodistribution Studies (Table 5)

Biodistribution studies on MDP bone scanning agent have shown that, once reconstituted with Tc-99m, it lasts only several hours. After that time, the agent dissociates, leaving unacceptibly high proportion of unbound Tc in the preparation, impairing or negating the quality of the resulting scan. After allowing 3 reconstituted MDP kits (New England Nuclear) to stand about 24 hours, each was filtered and the product used in a biodistribution study. The results show virtually no difference between the freshly prepared product and the filtered, rejuvenated product prepared in accordance with this invention.

Figure 2:
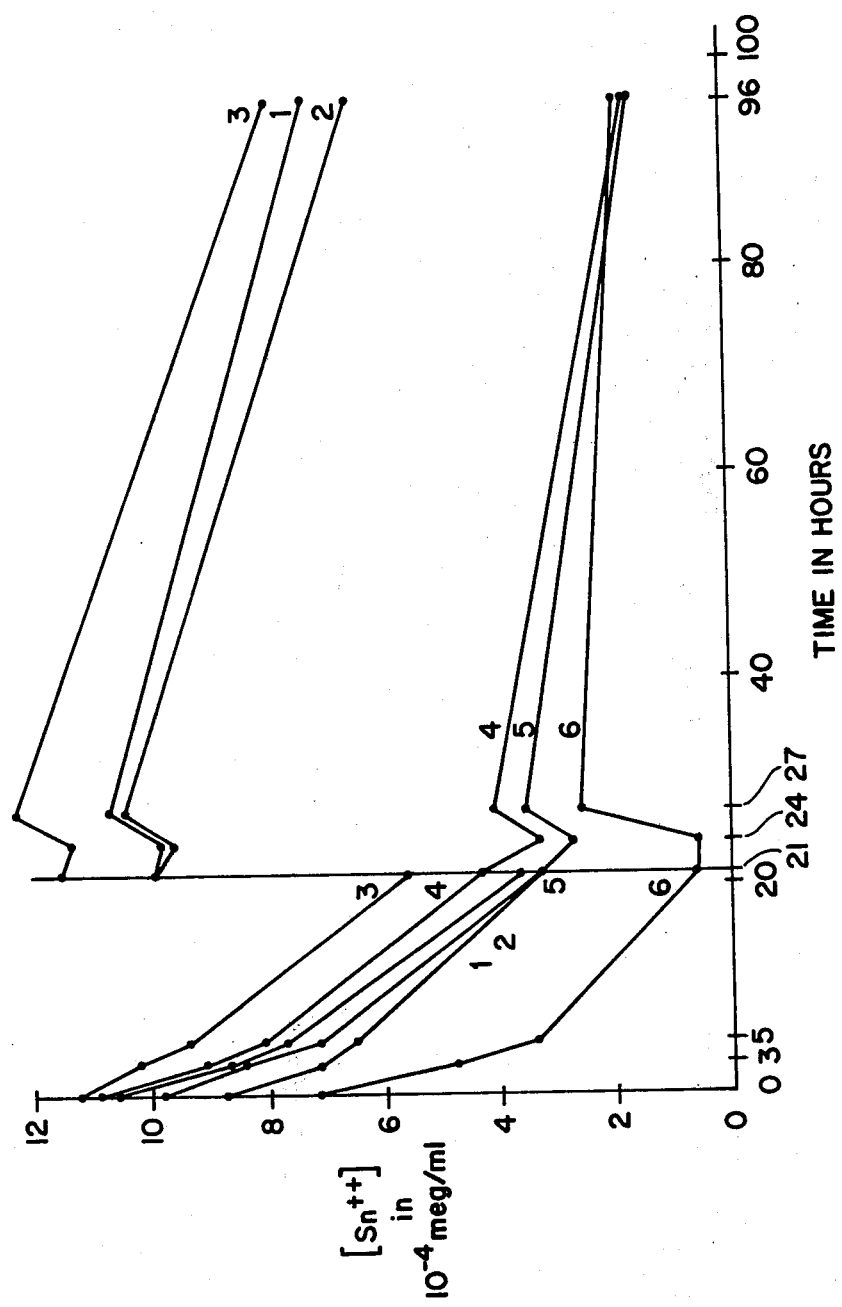
FIG. 2 is a graph showing stannous ion concentration as a function of time both prior to and subsequent to the filtering in accordance with this invention.

Time-Dependent $Sn^{++}$ Levels in Osteolite Kits (FIG. 2)

$Sn^{++}$ is the reducing agent in almost all Tc radiopharmaceutical kits. New England Nuclear's Osteolite kit was analyzed for $Sn^{++}$ as a function of time after reconstitution in accordance with this invention. The $Sn^{++}$ levels declined gradually but steadily after the time of reconstitution. Of six kits in this experiment, three were filtered (Nos. 1, 2 and 3) in accordance with this invention after standing 21 hours, while kits 4, 5 and 6 were not filtered. In these kits, $Sn^{++}$ levels returned to just about their initial levels. As the test continued over the next two days, the filtered preparations showed a similar but much slower decline in $Sn^{++}$ compared to the initial date.

TABLE 1

| Filter Number | $Sn^{++}$ Output of Filter Eluate Milliequivalents of $Sn^{++}$ per milliliter × $10^{-3}$ | | | |
|---|---|---|---|---|
| | 1st ml | 2nd ml | 3rd ml | 4th ml |
| 1 | 1.6 | 0.5 | 0.2 | |
| 2 | 1.9 | 0.8 | 0.2 | 0.1 |
| 3 | 1.0 | 0.4 | 0.2 | 0.1 |

TABLE 2

Efficiency of Filter for Removing Tc-Impurities

| Impurity | Percentage Removed* | |
|---|---|---|
| | Trial 1 | Trial 2 |
| $TcO_4^-$ | 99.79 | 99.60 |
| Reduced Hydrolyzed Technetium | 81.14 | 99.14 |

*Mean of three measurements

TABLE 3

Change in Tc-Radiopharmaceutical Quality After Filtration

| Radiopharmaceutical | Free $TcO_4^-$ | | Unexchangeable Tc* | |
|---|---|---|---|---|
| | before | after | before | after |
| Tc-MDP | 34.12 | 1.35 | 53.44 | 76.69 |
| Tc-DTPA | 12.58 | 0.08 | 83.43 | 96.38 |

*Unexchangeable Tc is the percentage of Tc-99m that is eluted from a regular Sephadex column in the peak which corresponds to the respective Tc-complex.

TABLE 4

Effect of Filtration at 21 Hours After Formulation on Free $TcO_4^-$ in Tc-MDP Aged 96 Hours

| Preparation | | % Free $TcO_4^-$ | |
|---|---|---|---|
| | | at 5 hours | at 96 hours |
| Filtered after 21 hours | 1 | 99.33 | 99.79 |
| | 2 | 99.46 | 99.26 |
| | 3 | 99.54 | 99.35 |
| | $\bar{x}$ | 99.44 | 98.80 |
| Not filtered | 4 | 99.64 | 86.51 |
| | 5 | 99.32 | 91.29 |
| | 6 | 98.46 | 59.31 |
| | $\bar{x}$ | 99.14 | 79.04 |

TABLE 5

Biodistribution of Tc 99m in Mice at 30 Minutes - Comparison of Filtered and Unfiltered Product

| | % Injected Dose per Organ or Mean of 3 Animals ± Standard Deviation | |
|---|---|---|
| Organ Tissue | unfiltered | filtered |
| Liver | 0.37 ± 0.34 | 0.29 ± 0.06 |
| Stomach & Intestines | 0.40 ± 0.08 | 0.38 ± 0.06 |
| Kidneys | 0.38 ± 0.08 | 0.44 ± 0.16 |
| Skeletal | 44.78 ± 8.00 | 45.41 ± 8.59 |
| Muscle | 1.86 ± 0.56 | 3.43 ± 1.52 |
| Blood | 0.65 ± 0.07 | 0.59 ± 0.23 |

We claim:

1. The process of purifying a composition labeled with technetium-99m and containing unbound reduced technetium impurity and/or pertechnetate impurity which comprises contacting said labeled composition with a solid particulate substrate containing stannous phthalate precipitated from a saturated solution and a secondary antioxidant, said substrate being capable of binding a technetate ion and capable of retaining unbound reduced technetium impurity and recovering purified labeled composition.

2. The process of claim 1 wherein said secondary antioxidant is gentisic acid.

3. The process of claim 1 wherein said secondary antioxidant is ascorbic acid.

4. The process of claim 1 wherein said particulate substrate is cross-linked dextran.

5. The process of claim 1 wherein said composition is $^{99m}$Tc-methylene diphosphonate.

6. The process of claim 1 wherein said composition is $^{99m}$-Tc-diethylenediaminepentaacetic acid.

7. Apparatus for purifying a composition labeled with technetium-99m which comprises a closed container having an inert non-oxidizing atmosphere and containing a solid particulate substrate capable of binding technetate ion and capable of retaining unbound reduced technetium impurity, stannous phthalate precipitated from a saturated solution and a secondary antioxidant.

8. The apparatus of claim 7 wherein said secondary antioxidant is gentistic acid.

9. The apparatus of claim 7 wherein said secondary antioxidant is ascorbic acid.

10. The apparatus of any one of claims 7, 8 or 9 wherein said particulate substrate is cross-linked dextran.

11. The process of claim 1 wherein said composition is $^{99m}$Tc-protein.

* * * * *